United States Patent
Bao

(10) Patent No.: US 10,702,230 B2
(45) Date of Patent: Jul. 7, 2020

(54) METHOD AND SYSTEM FOR GENERATING A PHASE CONTRAST IMAGE

(71) Applicant: SHANGHAI UNITED IMAGING HEALTHCARE CO., LTD., Shanghai (CN)

(72) Inventor: Yuan Bao, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 175 days.

(21) Appl. No.: 16/024,003

(22) Filed: Jun. 29, 2018

(65) Prior Publication Data
US 2019/0090832 A1 Mar. 28, 2019

Related U.S. Application Data

(63) Continuation of application No. PCT/CN2017/102973, filed on Sep. 22, 2017.

(51) Int. Cl.
| | | |
|---|---|---|
| A61B 6/00 | (2006.01) | |
| A61B 5/00 | (2006.01) | |
| A61B 6/04 | (2006.01) | |
| A61B 6/03 | (2006.01) | |

(52) U.S. Cl.
CPC ............ *A61B 6/484* (2013.01); *A61B 5/7267* (2013.01); *A61B 6/0407* (2013.01); *A61B 6/5211* (2013.01); *A61B 5/7207* (2013.01); *A61B 6/03* (2013.01); *A61B 6/5235* (2013.01); *A61B 6/56* (2013.01); *A61B 2576/00* (2013.01); *G06T 2207/10081* (2013.01); *G06T 2207/30004* (2013.01)

(58) Field of Classification Search
CPC .. A61B 6/00; A61B 6/04; A61B 6/484; A61B 6/0407; A61B 6/5235; A61B 5/7207; G06T 2207/30004; G06T 2207/10081
USPC ................................................ 378/62, 210
See application file for complete search history.

(56) References Cited

U.S. PATENT DOCUMENTS

| | | |
|---|---|---|
| 2004/0109530 A1 | 6/2004 | Amitani et al. |
| 2016/0310082 A1 | 10/2016 | Rajamani et al. |
| 2017/0091933 A1 | 3/2017 | Koehler et al. |

FOREIGN PATENT DOCUMENTS

CN 106373168 A 2/2017

OTHER PUBLICATIONS

International Search Report in PCT/CN2017/102973 dated Jun. 4, 2018, 4 pages.
Written Opinion in PCT/CN2017/102973 dated Jun. 4, 2018, 4 pages.

*Primary Examiner* — Jurie Yun
(74) *Attorney, Agent, or Firm* — Metis IP LLC

(57) ABSTRACT

A system and method for generating a phase contrast image based on an absorption contrast image are provided. The method may include obtaining an absorption contrast image of a first object. The method may further include obtaining a phase contrast image generation model, wherein the phase contrast image generation model may be associated with at least one sample absorption contrast image and at least one sample phase contrast image of a second object. The method may further include executing the phase contrast image generation model to generate a phase contrast image of the first object based on the absorption contrast image of the first object.

20 Claims, 9 Drawing Sheets

… (1)

METHOD AND SYSTEM FOR GENERATING A PHASE CONTRAST IMAGE

CROSS-REFERENCE TO RELATED APPLICATIONS

This application is a continuation of international Application No. PCT/CN2017/102973, filed on Sep. 22, 2017, designating the United States of America, the entire contents of which are hereby incorporated by reference.

TECHNICAL FIELD

This disclosure generally relates to a method and system for X-ray imaging, and more particularly, to a method and system for generating a phase contrast image based on an absorption contrast image.

BACKGROUND

X-ray imaging is commonly used in medical diagnosis for revealing conditions of organs or tissues of a patient. Absorption contrast imaging is a simple and common X-ray imaging technique, and it normally produces high-quality images of hard tissues and low-quality images of soft tissues. A different X-ray imaging technique, phase contrast imaging, may produce images of soft tissues with improved quality. At present, phase contrast imaging may be conducted using a phase contrast imaging device, which is expensive and inconvenient. Moreover, the current phase contrast imaging device usually has a small field of view (FOV) compared to a normal X-ray imaging device, and thus produces a phase contrast image of a limited size. Hence, it is desirable to find a way of obtaining a phase contrast image of any desired size without directly using the phase contrast imaging device.

SUMMARY

According to an aspect of the present disclosure, a system is provided. The system may include a storage device storing a set of instructions and at least one processor in communication with the storage device. When the at least one processor executes the set of instructions, the system may be directed to obtain an absorption contrast image of a first object. The system may be further directed to obtain a phase contrast image generation model, wherein the phase contrast image generation model may be associated with at least one sample absorption contrast image and at least one sample phase contrast image of a second object. The system may be further directed to execute the phase contrast image generation model to generate a phase contrast image of the first object based on the absorption contrast image of the first object.

According to another aspect of the present disclosure, a method is provided. The method may be implemented on a computing device having a storage device storing a set of instructions, and at least one processor communicated with the storage device. The method may include obtaining an absorption contrast image of a first object. The method may further include obtaining a phase contrast image generation model, wherein the phase contrast image generation model may be associated with at least one sample absorption contrast image and at least one sample phase contrast image of a second object. The method may further include executing the phase contrast image generation model to generate a phase contrast image of the first object based on the absorption contrast image of the first object.

According to another aspect of the present disclosure, a system is provided. The system may include an acquisition module and a processing module. The acquisition module may be configured to obtain an absorption contrast image of a first object. The acquisition module may be further configured to obtain a phase contrast image generation model, wherein the phase contrast image generation model may be associated with at least one sample absorption contrast image and at least one sample phase contrast image of a second object. The processing module may be configured to execute the phase contrast image generation model to generate a phase contrast image of the first object based on the absorption contrast image of the first object.

According to another aspect of the present disclosure, a non-transitory computer readable medium is provided. The non-transitory computer readable medium may include executable instructions that when executed by at least one processor of an electronic device, directs the at least one processor to perform actions. The actions may include obtaining an absorption contrast image of a first object. The actions may further include obtaining a phase contrast image generation model, wherein the phase contrast image generation model may be associated with at least one sample absorption contrast image and at least one sample phase contrast image of a second object. The actions may further include executing the phase contrast image generation model to generate a phase contrast image of the first object based on the absorption contrast image of the first object.

In some embodiments, the absorption contrast image of the first object and the at least one sample absorption contrast image of the second object may be obtained by scanning with a same scanning parameter and reconstruction with a same reconstruction parameter.

In some embodiments, the phase contrast image generation model may be a neural network model.

In some embodiments, the method may further include obtaining a dark field image generation model, and executing the dark field image generation model based on the absorption contrast image of the first object to generate a dark field image of the first object.

In some embodiments, the dark field image generation model may be trained based on the at least one sample absorption contrast image of the second object and at least one sample dark field image of the second object.

According another aspect of the present disclosure, a system is provided. The system may include a storage device storing a set of instructions and at least one processor in communication with the storage device. When the at least one processor executes the set of instructions, the system may be directed to obtain a preliminary model. The system may be further directed to obtain at least one pair of training images of an object including a sample absorption contrast image and a corresponding sample phase contrast image of the object. The system may be further directed to train the preliminary model based on the at least one pair of training images to generate a phase contrast image generation model.

According to another aspect of the present disclosure, a method is provided. The method may be implemented on a computing device having a storage device storing a set of instructions, and at least one processor communicated with the storage device. The method may include obtaining a preliminary model. The method may further include obtaining at least one pair of training images of an object including a sample absorption contrast image and a corresponding sample phase contrast image of the object. The method may further include training the preliminary model based on the at least one pair of training images to generate a phase contrast image generation model.

According to another aspect of the present disclosure, a system is provided. The system may include an acquisition module and a training module. The acquisition module may be configured to obtain a preliminary model. The acquisition module may be further configured to obtain at least one pair of training images of an object including a sample absorption contrast image and a corresponding sample phase contrast image of the object. The training module may be configured to train the preliminary model based on the at least one pair of training images to generate a phase contrast image generation model.

According to another aspect of the present disclosure, a non-transitory computer readable medium is provided. The non-transitory computer readable medium may include executable instructions that, when executed by at least one processor of an electronic device, directs the at least one processor to perform actions. The actions may include obtaining a preliminary model. The actions may further include obtaining at least one pair of training images of an object including a sample absorption contrast image and a corresponding sample phase contrast image of the object. The actions may further include training the preliminary model based on the at least one pair of training images to generate a phase contrast image generation model.

In some embodiments, the obtaining the pair of training images of the second object may further include obtaining a sample photon signal of the object and separating the sample photon signal into a sample absorption contrast signal and a sample phase contrast signal. The obtaining the pair of training images of the second object may further include generating the sample absorption contrast image based on the sample absorption contrast signal and generating the corresponding sample phase contrast image based on the sample phase contrast signal.

In some embodiments, the obtaining the sample photon signal of the second object may further include scanning the object using a synchrotron light source.

In some embodiments, the object may be a simulated object. The generating the at least one sample photon signal may further include performing at least one numerical simulation on the object to obtain the at least one sample photon signal.

In some embodiments, the phase contrast image generation model may be a neural network model.

In some embodiments, the preliminary model may be trained using a deep learning algorithm.

In some embodiments, the training the preliminary model based on the at least one pair of training images to generate a phase contrast image generation model may further include executing the preliminary model based on the sample absorption contrast image to generate at least one output image. The training the preliminary model based on the at least one pair of training images to generate a phase contrast image generation model may further include training the preliminary model by minimizing the difference between the at least one output image and the corresponding sample phase contrast image to generate the phase contrast image generation model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
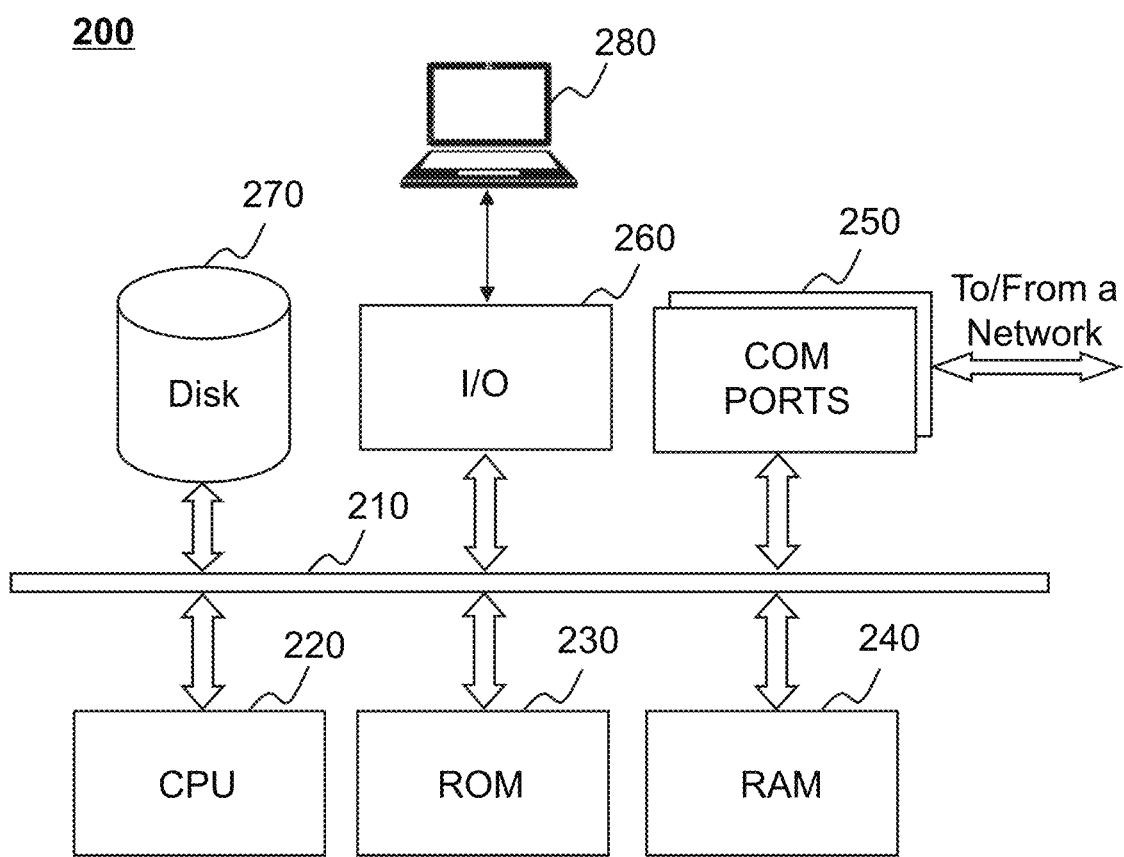
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., CPU 220 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The present disclosure relates to a method and system for generating a phase contrast image. The method illustrates a way of generating the phase contrast image based on an absorption contrast image and a phase contrast image generation model. The present disclosure also includes a system and method for training a phase contrast image generation model based on a neural network model.

Figure 1:
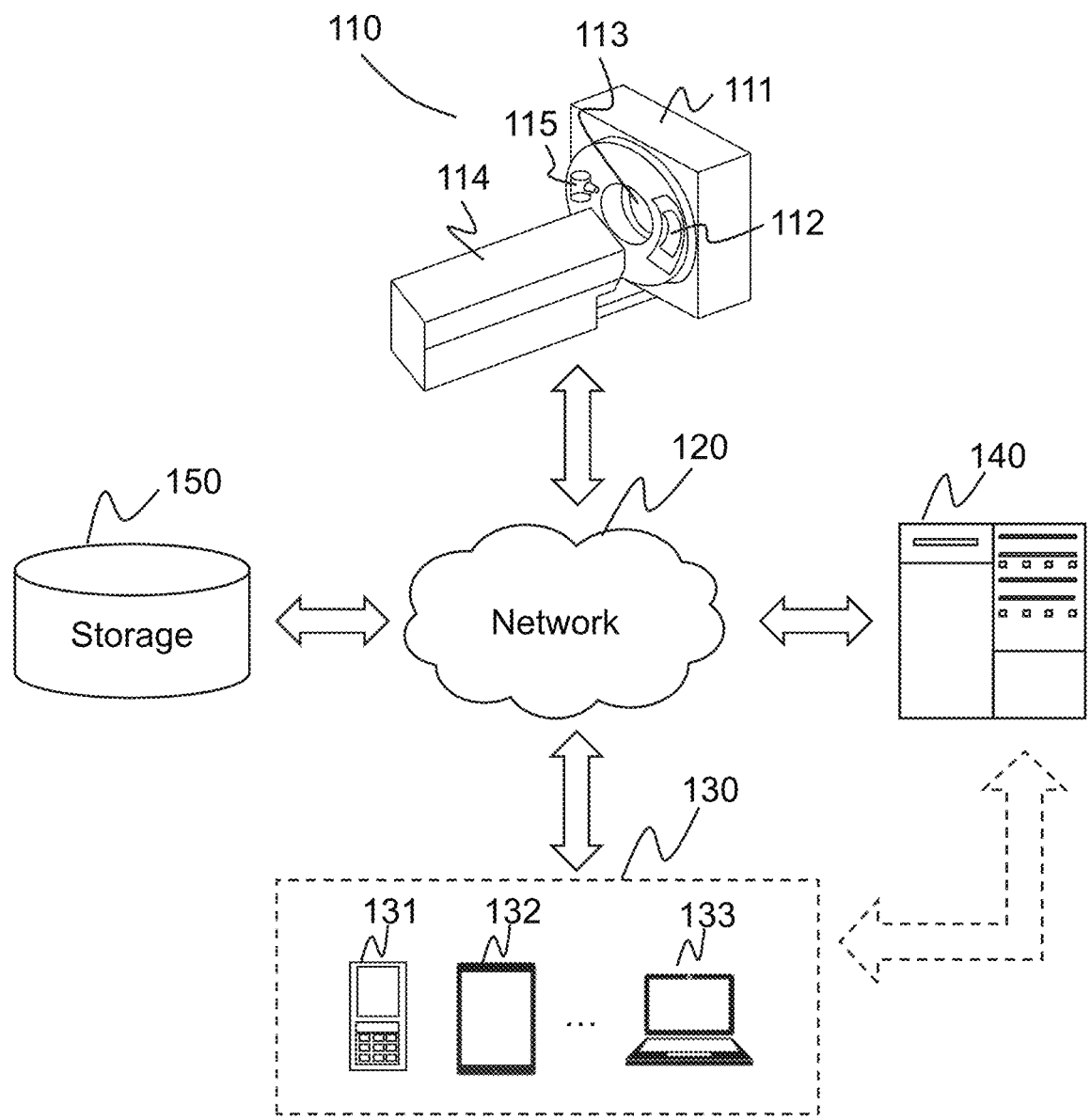
FIG. 1 is a schematic diagram illustrating an exemplary imaging system according to some embodiments of the present disclosure.

FIG. 1 is a schematic diagram illustrating an exemplary imaging system according to some embodiments of the present disclosure. As shown in FIG. 1, the imaging system 100 may include a scanner 110, a network 120, one or more terminals 130, a processing device 140, and a storage 150. All the components in the imaging system 100 may be interconnected via the network 120.

The scanner 110 may scan an object and generate scanned data relating to the object. In some embodiments, the scanner 110 may be a medical imaging device, for example, an X-ray device, a computed tomography (CT) device, a digital radiography (DR) device, etc. The scanner 110 may include a gantry 111, a detector 112, a detecting region 113, and a table 114. In some embodiments, the scanner 110 may also include a radioactive scanning source 115. The gantry 111 may support the detector 112 and the radioactive scanning source 115. An object may be placed on the table 114 for scanning. The radioactive scanning source 115 may emit radioactive rays to the object. The detector 112 may detect radiation events (e.g., X-ray) emitted from the detecting region 113. In some embodiments, the scanner 110 may be a CT scanning device and the detector 112 may include an electric circuit for detecting and receiving X-ray signals.

The network 120 may include any suitable network that can facilitate exchange of information and/or data for the imaging system 100. In some embodiments, one or more components of the imaging system 100 (e.g., the scanner 110, the terminal 130, the processing device 140, the storage 150, etc.) may communicate information and/or data with one or more other components of the imaging system 100 via the network 120. For example, the processing device 140 may obtain image data from the scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage 150. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage 150 via the network 120. As another example, the processing device 140 may be directly connected to the scanner 110, the terminal 130 and/or the storage 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage 150 may store data, instructions, and/or any other information. In some embodiments, the storage 150 may store data obtained from the terminal 130 and/or the processing device 140. In some embodiments, the storage 150 may store data and/or instructions that the processing device 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing device 140, the terminal 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing device 140, the terminal 130, etc.). In some embodiments, the storage 150 may be part of the processing device 140.

FIG. 2 is a schematic diagram illustrating an exemplary hardware and software components of a computing device according to some embodiments of the present disclosure.

The computing device 200 may be a general purpose computer or a special purpose computer, both may be used to implement an imaging system of the present disclosure. In some embodiments, the processing device 140 may be implemented on the computing device 200, via its hardware, software program, firmware, or a combination thereof. For example, the computing device 200 may obtain a preliminary model. The computing device 200 may train the preliminary model based on at least one sample absorption contrast image and at least one sample phase contrast image to obtain a trained model. The computing device 200 may execute a phase contrast image generation model (e.g., the trained model) to generate a phase contrast image based on an absorption contrast image. Although only one such computer is shown, for convenience, the computer functions relating to the CT imaging as described herein may be implemented in a distributed manner on a number of similar platforms, to distribute the processing load.

The computing device 200, for example, may include COM ports 250 connected to and from a network connected thereto to facilitate data communications. The computing device 200 may also include a central processing unit (CPU) 220, in the form of one or more processors, for executing program instructions. The exemplary computer platform may include an internal communication bus 210, program storage and data storage of different forms, for example, a disk 270, and a read only memory (ROM) 230, or a random access memory (RAM) 240, for various data files to be processed and/or transmitted by the computer. The exemplary computer platform may also include program instructions stored in the ROM 230, RAM 240, and/or another type of non-transitory storage medium to be executed by the CPU 220. The methods and/or processes of the present disclosure may be implemented as the program instructions. The computing device 200 also includes an I/O component 260, supporting input/output between the computer and other components therein such as user interface elements 280. The computing device 200 may also receive programming and data via network communications.

The computing device 200 may also include a hard disk controller communicated with a hard disk, a keypad/keyboard controller communicated with a keypad/keyboard, a serial interface controller communicated with a serial peripheral equipment, a parallel interface controller communicated with a parallel peripheral equipment, a display controller communicated with a display, or the like, or any combination thereof.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, if in the present disclosure the CPU and/or processor of the computing device 200 executes both operation A and operation B, it should be understood that operation A and operation B may also be performed by two different CPUs and/or processors jointly or separately in the computing device 200 (e.g., the first processor executes operation A and the second processor executes operation B, or the first and second processors jointly execute operations A and B).

Figure 3:
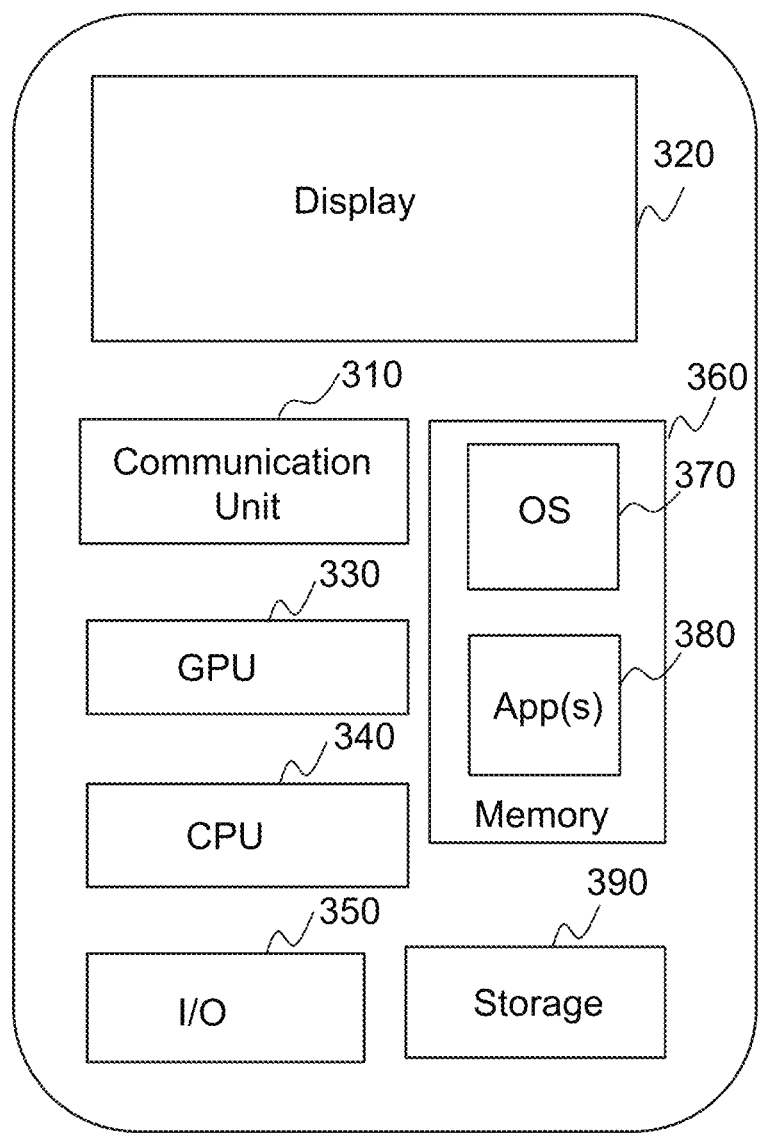
FIG. 3 is a schematic diagram illustrating exemplary hardware and/or software components of an exemplary mobile device that is configured to implement a specific system disclosed in the present disclosure.

FIG. 3 is a schematic diagram illustrating an exemplary hardware and/or software components of an exemplary mobile device that is configured to implement a specific system disclosed in the present disclosure. As illustrated in FIG. 3, the mobile device 300 may include an antenna 310, a display 320, a graphic processing unit (GPU) 330, a CPU 340, an I/O 350, a storage 360, and a memory 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 390 from the storage 360 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120. In some embodiments, a user may input parameters to the imaging system 100, via the mobile device 300, for the imaging system 100 to execute a phase contrast image generation model. Alternatively or additionally, a user may input parameters to the imaging system 100, via the mobile device 300, for the imaging system 100 to train a preliminary model.

In order to implement various modules, units and their functions described above, a computer hardware platform may be used as hardware platforms of one or more elements (e.g., the processing device 140 and/or other sections of the system 100 described in FIG. 1). Since these hardware elements, operating systems and program languages are common; it may be assumed that persons skilled in the art may be familiar with these techniques and they may be able to provide information required in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computer device. Thus, extra explanations are not described for the Figures.

Figure 4:
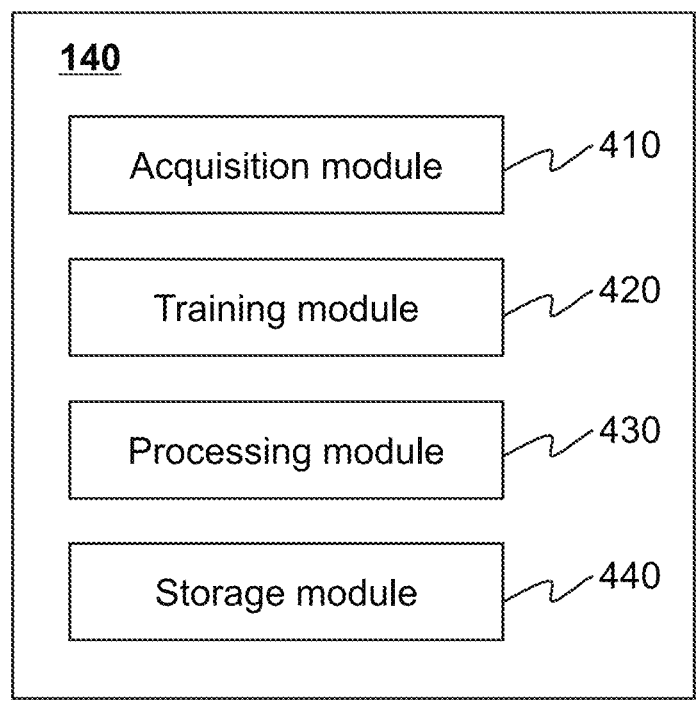
FIG. 4 is a schematic diagram illustrating an exemplary processing device according to some embodiments of the present disclosure.

FIG. 4 is a schematic diagram illustrating an exemplary processing device according to some embodiments of the present disclosure. The processing device 140 may include an acquisition module 410, a training module 420, a processing module 430, and a storage module 440.

The acquisition module 410 may obtain an image, a model, or other information. In some embodiments, the image may include an absorption contrast image, a phase contrast image, a dark field image, or the like, or any combination thereof. The model may include a phase contrast image generation model, a dark field image generation model, or the like, or any combination thereof.

The training module 420 may be configured to train a preliminary model and obtain a trained model. The preliminary model and/or the trained model may be a neural network model. The preliminary model may be trained using a deep learning algorithm. The preliminary model and/or the trained model may be executed to generate a phase contrast image based on an absorption contrast image. In some embodiments, the training module 420 may include an acquisition unit 610, a separation unit 620, a training unit 630, and a processing unit 640. More descriptions regarding the training module 420 may be found elsewhere in the present disclosure. See, e.g., FIG. 6 and the descriptions thereof.

The processing module 430 may be configured to execute a model and/or generate an image. In some embodiments, the processing module 430 may execute the phase contrast image generation model to generate a phase contrast image based on an absorption contrast image. When executing the phase contrast image generation model, the processing module 430 may apply the model to an absorption contrast image. In a case that specialized models corresponding to different organs and tissues of the object are generated, the processing module 430 may first identify the organs and/or tissues in the absorption contrast image and input the absorption contrast image to the corresponding model. For example, for an absorption contrast image relating to a head of a patient, a phase contrast image generation model for a head may be selected and used by the processing module 430.

In some embodiments, the processing module 430 may execute a dark field image generation model to generate a dark field image based on an absorption contrast image. The dark field image generation model may be trained based on at least one sample absorption contrast image and at least one sample dark field image.

The storage module 440 may be configured to store the information during the process of generating a phase contrast image. In some embodiments, the storage module 410 may store an absorption contrast image of a first object, at least one sample absorption contrast image of a second object, at least one sample phase contrast image of the second object, or the like, or any combination thereof. Other modules of the processing device 140 (e.g., the acquisition module 410, the training module 420, or the processing module 430) may access the information stored in the storage module 440.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more modules. For example, the acquisition module 410 and the processing module 430 may be combined as a single module that performs the corresponding functions. As another example, the training module 420 and the processing module 430 may be integrated into a single module that performs the corresponding functions. As a further example, the training module 420 may be omitted and models may be trained by an external device. Such models may be stored in, e.g., the storage module 440, or retrieved from an external device by, e.g., the acquisition module 410.

Figure 5:
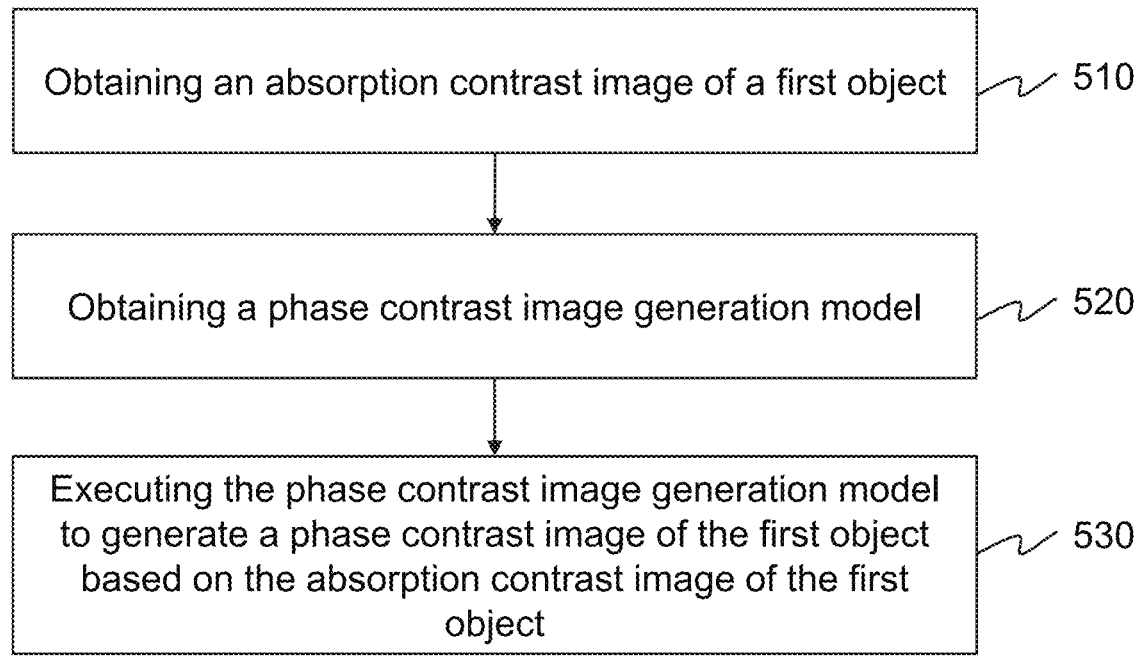
FIG. 5 is a flowchart illustrating an exemplary process for determining a phase contrast image according to some embodiments of the present disclosure.

FIG. 5 is a flowchart illustrating an exemplary process for determining a phase contrast image according to some embodiments of the present disclosure. The process 500 may be executed by the processing device 140. For example, the process 500 may be implemented as a set of instructions (e.g., an application) stored in the storage, e.g., ROM 230, RAM 240, the storage 150, the storage 390, the storage module 440, a storage device external to and accessible by the imaging system 100. The CPU 220 may execute the set of instructions, and when executing the instructions, it may be configured to perform the process 500.

In 510, the acquisition module 410 may obtain an absorption contrast image of a first object. In some embodiments, the first object may include a specific portion of a body, a specific organ, or a specific tissue, such as the head, the brain, the neck, the body, a shoulder, an arm, the thorax, the heart, the stomach, a blood vessel, a soft tissue, a knee, a foot, or the like, or any combination thereof. In some embodiments, the object may be a human patient, or a portion thereof. The object may be an animal, a substance, a material, or the like, or any combination thereof. In some embodiments, the absorption contrast image may be obtained via an X-ray imaging device, for example, a digital radiography (DR) device, a computed tomography (CT) device, a C-arm X-ray machine, a four-dimensional CT device, or the like, or any combination thereof. An absorption contrast image may be a shadowgraph. The contrast of grey values of pixels in the absorption contrast image may be generated due to different attenuation coefficient (also referred to as attenuation rate) of various parts in the first object. For example, different parts of an object may attenuate or absorb the X-ray dose differently based on their attenuation coefficient. A detector (e.g., the detector 112) may detect the intensities of X-ray that passes through different parts of the object and impinges on the detector 112. An absorption contrast image of the object may be reconstructed based on the different intensities of X-ray detected by the detector.

In some embodiments, the absorption contrast image may be of any size. For example, the length (or width) of the absorption contrast image may vary between 3 cm and 100 cm. Merely by way of example, the length (or width) of the absorption contrast image may be 15 cm, 30 cm, 40 cm, 44 cm, 50 cm, 60 cm, etc. In some embodiments, the size of the absorption contrast image of the first object and the size of a sample absorption contrast image (that may be used to train the model applicable to the absorption contrast image) may be different. For example, a sample absorption contrast image may be a small image with a length (or width) varying between 3 cm and 15 cm. The absorption contrast image may be a large image with a length (or width) varying between 5 cm and 100 cm. The absorption contrast image may include an axial image, a coronal image, a sagittal image, or the like, or any combination thereof. The absorption contrast image may be a three-dimensional (3D) image including a stack of two-dimensional (2D) images.

In 520, the acquisition module 410 may obtain a phase contrast image generation model. The phase contrast image generation model may be employed to generate a phase contrast image based on the absorption contrast image. In some embodiments, the phase contrast image generation model may be generated by training based on at least one sample absorption contrast image and at least one sample phase contrast image of a second object that is different from the first object being imaged. The absorption contrast image of the first object and the at least one sample absorption contrast image of the second object may be obtained by scanning with one or more same scanning parameters and reconstruction based on one or more same reconstruction parameters. The scanning parameters may include a tube voltage, a tube current, a tube frequency, a scanning mode, the duration of a scan, or the like, or any combination thereof. The reconstruction parameters may include an image layer thickness in reconstruction, a type of filter, filtering strength, or the like, or any combination thereof. In some embodiments, the absorption contrast image of the first object and the at least one sample absorption contrast image of the second object may be obtained by scanning using a radiation source of a same or similar energy level. For example, both the absorption contrast image of the first object and the at least one sample absorption contrast image of the second object may be obtained by scanning using a radiation source of 120 kV.

In some embodiments, the phase contrast image generation model may be a neural network model. The neural network model may include an artificial neural network (ANN) model, a biological neural network model, a convolutional neural network (CNN), or the like, or any combination thereof. More descriptions regarding the training of the phase contrast image generation may be found elsewhere in the present disclosure. See, e.g., FIG. 7 and the descriptions thereof. More descriptions regarding the structure of a neural network may be found elsewhere in the present disclosure. See, e.g., FIG. 8 and the descriptions thereof.

In 530, the processing module 430 may execute the phase contrast image generation model to generate a phase contrast image of the first object based on the absorption contrast image of the first object. The phase contrast image may correspond to the first object. For example, if the absorption contrast image is an absorption contrast image of a head, the phase contrast image may be a phase contrast image of the head. In some embodiments, the phase contrast image generation model may be a universal model or a specialized model. A universal model may be used to generate a phase contrast image corresponding to one or more of multiple types of absorption contrast images of multiple objects or multiple sections of an object. The universal model may be trained based on a plurality of sample absorption contrast images and a plurality of sample phase contrast images that are associated with one or more of different sections of a type of object (e.g., a human body, a type of animals (e.g., dogs, cats)). In some embodiments, the plurality of sample absorption contrast images and the plurality of sample phase contrast images that are used in training may collectively cover a whole human body. A specialized model may correspond to a specific object or body section. For example, a specialized model of a brain may be used for generating a phase contrast image of a brain based on an absorption contrast image of the brain. If an absorption contrast image of a chest is used with the specialized model of a brain, no phase contrast image may be generated or the generated phase contrast image may be of low quality. As another example, the use of a specialized model for a specific group of objects may be limited to processing images of objects of that group, e.g., for children of a certain age group, the use of the model may be limited to absorption contrast images of children of that age group. A specialized model may be trained based on sample absorption contrast images and sample phase contrast images relating to a particular object, or a particular section of an object, or objects of a certain group, or a particular section of objects of a certain group.

In some embodiments, the acquisition module 410 may obtain a dark field image generation model. The processing module 430 may execute the dark field image generation model to generate a dark field image based on the absorption contrast image. In some embodiments, the dark field image generation model may be trained based on the at least one sample absorption contrast image of the second object and at least one sample dark field image of the second object.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operations (e.g., an operation of storing intermediate or final results) may be added in the exemplary process 500.

Figure 6:
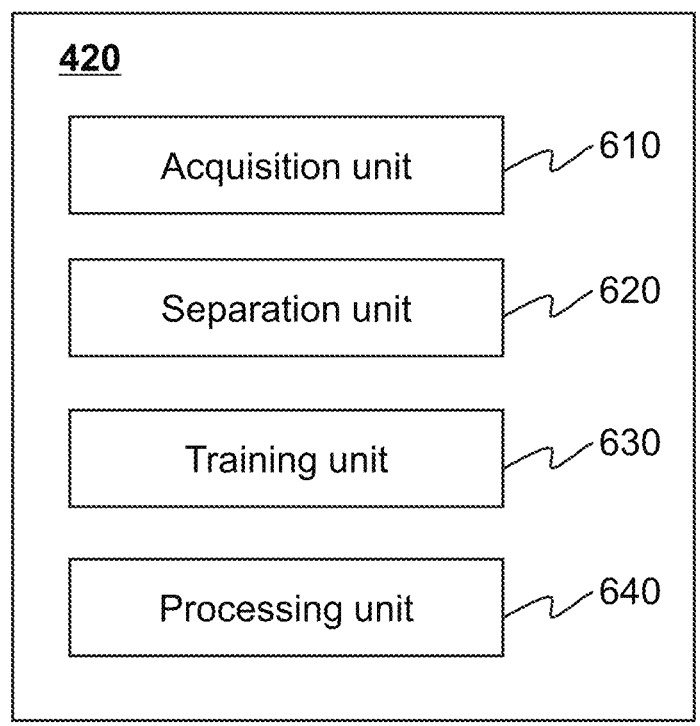
FIG. 6 is a schematic block diagram illustrating an exemplary training module according to some embodiments of the present disclosure.

FIG. 6 is a schematic block diagram illustrating an exemplary training module according to some embodiments of the present disclosure. As shown in FIG. 6, the training module 420 may include an acquisition unit 610, a separation unit 620, a training unit 630, and a processing unit 640.

The acquisition unit 610 may be configured to obtain a preliminary model. The preliminary model may be a general model with a default inner structure (also referred to as inner parameters). The acquisition unit 610 may obtain at least one sample photon signal. Alternatively or additionally, the acquisition unit 610 may obtain at least one sample absorption contrast image and at least one sample phase contrast image. In some embodiments, the acquisition unit 610 may obtain a half-trained model or a trained model.

The separation unit 620 may be configured to perform a separation operation. In some embodiments, the separation unit 620 may separate a photon signal into a sample absorption contrast signal and a sample phase contrast signal. In some embodiments, a photon signal may be separated by an information extraction technique. Exemplary information extraction techniques may include a phase-stepping technique, a reverse-projection technique, a Fourier transform technique, a window-Fourier-transform technique, a conjugate ray pairs algorithm, or the like, or any combination thereof.

The training unit 630 may be configured to train the preliminary model. The training unit 630 may train the preliminary model based on at least one sample absorption contrast image and at least one sample phase contrast image. The training unit 630 may train the preliminary model to generate a phase contrast image generation model. In some embodiment, the preliminary model may be trained using a deep learning algorithm. More descriptions regarding the process for training the preliminary model may be found elsewhere in the present disclosure. See, e.g., FIG. 7 and the descriptions thereof.

The processing unit 640 may be configured to process information generated or obtained and to generate a processing result accordingly. In some embodiments, the processing unit 640 may execute the preliminary model based on one of the at least one sample absorption contrast image to generate an output image. The processing unit 640 may determine a difference between the output image and the sample phase contrast image corresponding to the sample absorption contrast image. The processing unit 640 may determine whether a preset condition is satisfied.

Figure 7:
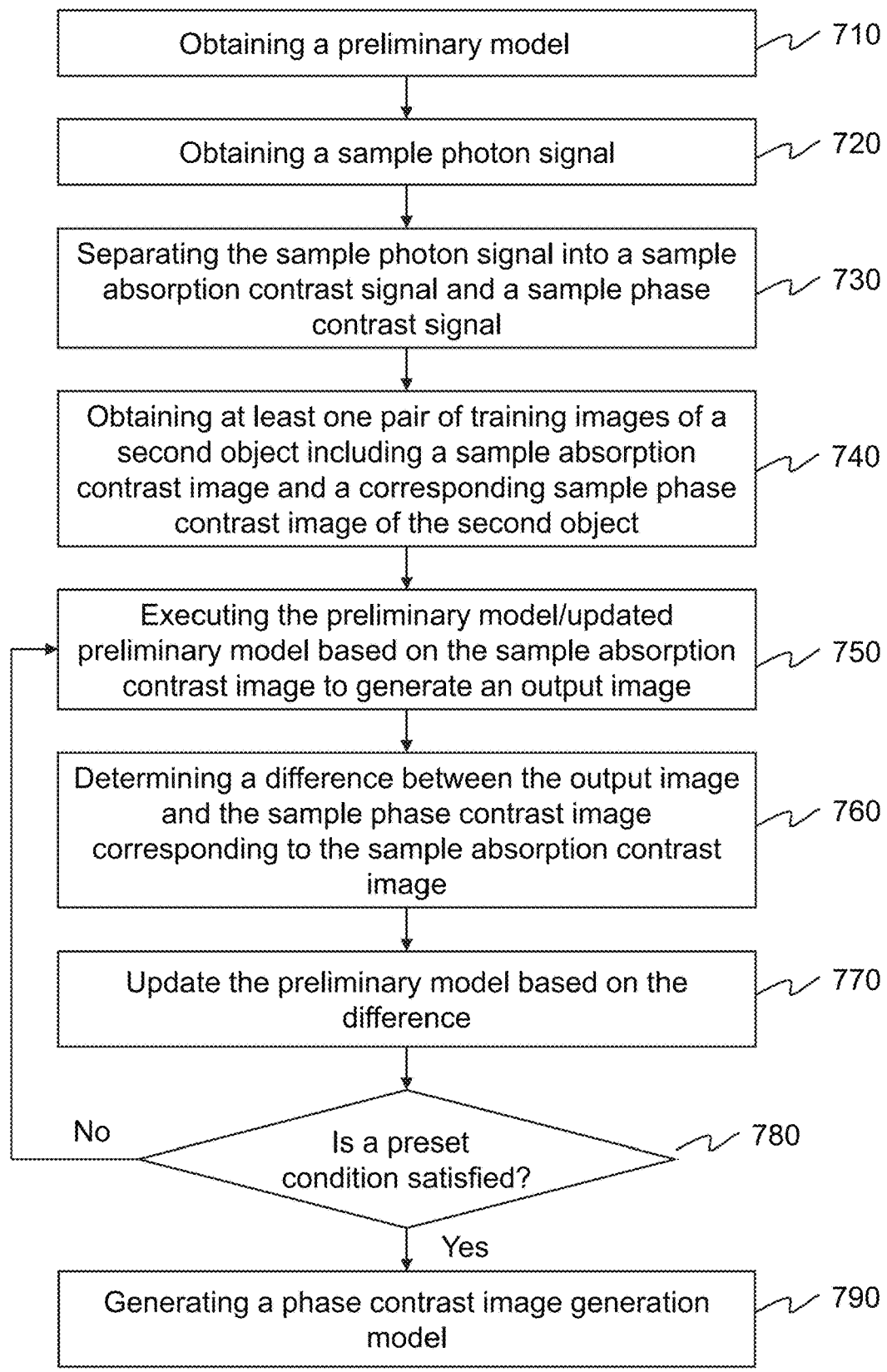
FIG. 7 is a flowchart illustrating an exemplary process for model training according to some embodiments of the present disclosure.

FIG. 7 is a flowchart illustrating an exemplary process for training a model according to some embodiments of the present disclosure. The process 700 may be executed by the processing device 140. For example, the process 700 may be implemented as a set of instructions (e.g., an application) stored in the storage 150, ROM 230, RAM 240, the storage 390, the storage module 440, and/or a storage device external to and accessible by the imaging system 100. The CPU 220 may execute the set of instructions, and when executing the instructions, it may be configured to perform the process 700. The operations of the illustrated process presented below are intended to be illustrative. In some embodiments, the process 700 may be accomplished with one or more additional operations not described and/or without one or more of the operations discussed. Additionally, the order in which the operations of the process as illustrated in FIG. 7 and described below is not intended to be limiting.

In 710, the acquisition unit 610 may obtain a preliminary model. The preliminary model may be trained to provide a phase contrast image generation model. In some embodiments, the preliminary model may be a neural network model. In some embodiments, the preliminary model may be predefined according to different situations. For example, the inner structure or the parameters of the preliminary model may be predefined according to one or more characteristics (e.g., size, complexity) of a specific object that the preliminary model (and/or a trained model) is associated with. In some embodiments, the preliminary model may be a phase contrast image generation model applicable for multiple objects, and the training process 700 may retrain the phase contrast image generation model for a desired group of objects or a section thereof.

In 720, the acquisition unit 610 may obtain at least one sample photon signal. A sample photon signal of an object may be processed to provide a sample absorption contrast signal and a sample phase contrast signal of the object. For example, a refractive index may be obtained based on a sample photon signal. The sample absorption contrast signal and the sample phase contrast signal may relate to the real and imaginary part of the refractive index, respectively.

Merely by way of example, the absorption contrast signal $\mu$ may be expressed as:

$$\mu = \frac{4\pi}{\lambda} \int \beta dz, \tag{1}$$

$$\beta = \frac{\lambda}{4\pi} \Sigma_k\ N_k u_k, \tag{2}$$

where $u_k$ denotes the absorption cross-sectional area, $\lambda$ denotes the wave length of X-ray, and k denotes the wave number.

The phase absorption contrast signal $\phi$ may be expressed as:

$$\phi = \frac{4\pi}{\lambda} \int \delta dz, \tag{3}$$

$$\delta = \frac{\lambda}{2\pi} \Sigma_k\ N_k p_k, \tag{4}$$

where $p_k$ denotes the phase shift cross-sectional area.

The refractive index may be expressed as:

$$n=1-\delta+i\beta, \quad (5)$$

where n denotes the refractive index (e.g., the refractive index of the object), δ, the real part of the refractive index, relates to the phase absorption contrast signal ϕ in formula (3), and β, the imaginary part of the refractive index, relates to the absorption contrast signal μ in formula (1).

In some embodiments, a sample photon signal may be obtained by scanning an object using a synchrotron light source. In some embodiments, the object may be a simulated object. At least one simulated scan may be performed on the simulated object to generate the at least one sample photon signal. For example, a numerical simulation (e.g., a Monte Carlo simulation) may be performed on the simulated object to generate the at least one sample photon signal.

In 730, the separation unit 620 may separate each of the at least one sample photon signal into a sample absorption contrast signal and a sample phase contrast signal. In some embodiments, a sample photon signal may be separated by an information extraction technique. Exemplary information extraction techniques may include a phase-stepping technique, a reverse-projection technique, a Fourier transform technique, a window-Fourier-transform technique, a conjugate ray pairs algorithm, or the like, or any combination thereof. The phase stepping algorithm may include a cross phase stepping algorithm, an electromagnetic phase stepping algorithm, etc.

In 740, the acquisition unit 610 may obtain at least one pair of training images including a sample absorption contrast image and a corresponding sample phase contrast image. As used herein, an absorption contrast image may be considered corresponding to a phase contrast image if at least part of the absorption contrast image and the phase contrast image is associated with a same object or a same section of an object. In some embodiments, the sample absorption contrast image and the sample phase contrast signals may be obtained by image reconstruction based on the sample absorption contrast signal and the corresponding sample phase contrast signal, respectively. In some embodiments, the sample absorption contrast signal and the corresponding sample phase contrast signal may be determined by the separation unit 620 based on a photon signal as described elsewhere. In some embodiments, the sample absorption contrast signal and the corresponding sample phase contrast signal may be acquired directly by scanning an object. In some embodiments, the sample absorption contrast signal and the corresponding sample phase contrast signal (or the corresponding sample absorption contrast image and sample phase contrast image) may be retrieved from an image library. In some embodiments, the sample absorption contrast image may correspond to the sample phase contrast image. For example, the sample absorption contrast image and the sample phase contrast image may correspond to the same object.

In some embodiments, the sample absorption contrast image and the sample phase contrast image of the object may be obtained separately. For example, the sample absorption contrast image of the object may be obtained via an X-ray imaging device, and the sample phase contrast image of the object may be obtained by an X-ray grating phase contrast imaging device. In some embodiments, when the object is a simulated object, the sample absorption contrast image and the sample phase contrast image of the object may be obtained by numerical simulations (e.g., a Monte Carlo simulation).

In some embodiments, the size of the absorption contrast image of an object being imaged and the size of a sample absorption contrast image (used to train the model) used to train the preliminary model may be different. For example, a sample absorption contrast image may be a small image with a length (or width) varying between 3 cm and 15 cm. The absorption contrast image of the object being imaged may be a large image with a length (or width) varying between 5 cm and 100 cm.

In some embodiments, the process 700 may be an iterative process. For example, the preliminary model may be trained by executing multiple iterations by the training unit 630. In each iteration, operations 750, 760, 770, and 780 may be executed with respect to a pair of sample absorption contrast image and a corresponding sample phase contrast image of a same object, and the preliminary model may be updated accordingly. The iterative process may end when a preset condition is satisfied in 780.

In 750, the processing unit 640 may execute the preliminary model or updated preliminary model based on a sample absorption contrast image to generate an output image. The output image may be an output phase contrast image corresponding to the sample absorption contrast image.

In 760, the processing unit 640 may determine a difference between the output image and the sample phase contrast image corresponding to the sample absorption contrast image. In some embodiments, the difference between the output image and the sample phase contrast image may be assessed in terms of a loss function. The loss function may include but not limited to an L1 norm loss function, an L2 norm loss function, a quadratic cost function, a cross-entropy loss function, a log-likelihood cost function, or the like, or any combination thereof.

In 770, the processing unit 640 may update the preliminary model (or further update an updated preliminary model) based on the difference. In some embodiments, the preliminary model may be updated by different strategies. For example, if the difference between the output image and the sample phase contrast image in the present iteration is less than a threshold (e.g., the difference determined in the preceding iteration), part or all parameters of the preliminary model may be updated. If the difference between the output image and the sample phase contrast image in the present iteration is great than the difference in the preceding iteration, the preliminary model is not updated in the current round of iteration.

In 780, the processing unit 640 may determine whether a preset condition is satisfied. If the preset condition is satisfied, the process 700 may proceed to 790; otherwise, the process 700 may proceed back to 750. In some embodiments, the preset condition may include training the preliminary model by all the sample absorption contrast images and the corresponding sample phase contrast images that are available. As another example, the preset condition may include that the difference between the out image and the sample phase contrast image is less than a threshold in one or more consecutive iterations. As a further example, the preset condition may include that the difference between the out image and the sample phase contrast image in the present iteration does not change in a preset number of iterations. As still a further example, the preset condition may be that the trained model converges indicated by, e.g., the parameters of the training model do not change or change within a range over a certain number of iterations.

In 790, the processing unit 640 may provide a trained model. The trained model may be the phase contrast image generation model used to generate a phase contrast image based on the absorption contrast image. More descriptions about using the trained model may be found in FIG. 5 and the related descriptions.

Figure 8:
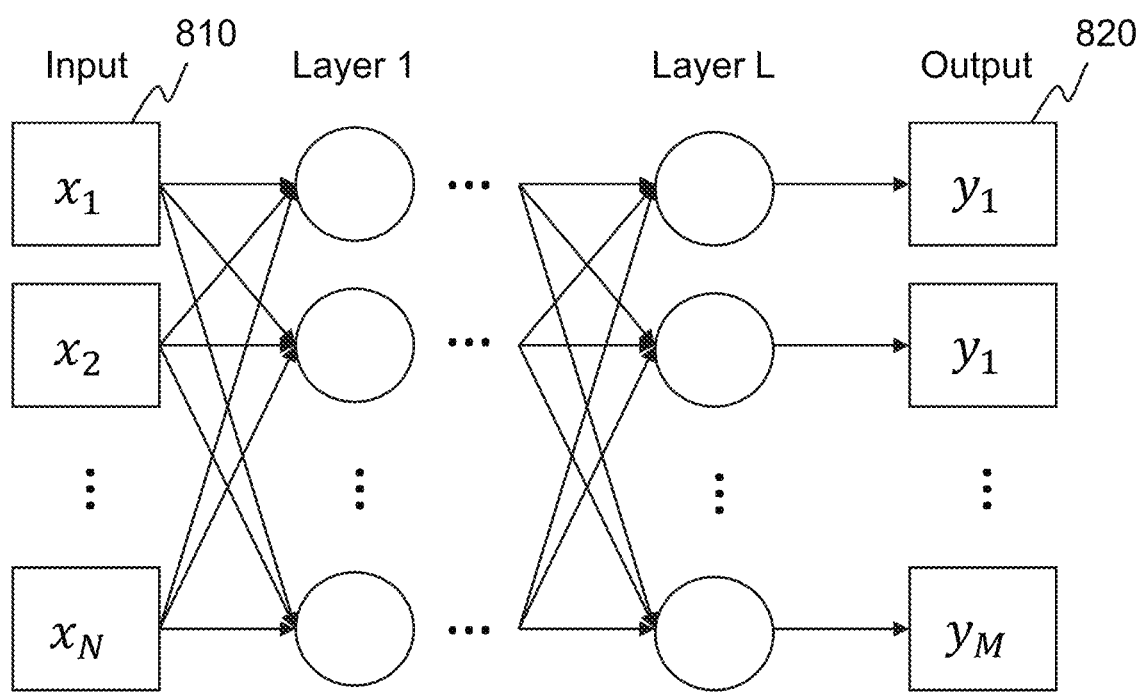
FIG. 8 is a schematic diagram illustrating the structure of an exemplary neural network model.

FIG. 8 is a schematic diagram illustrating the structure of an exemplary neural network model. The neural network model may be used to construct a phase contrast image generation model. In some embodiments, the neural network model may include an artificial neural network (ANN) model, a biological neural network (BNN) model, a convolutional neural network (CNN) model, or the like, or any combination thereof. Taking a CNN model as an example, the CNN model may be executed based on a collection of connected units called artificial neurons (analogous to axons in a biological brain). Each connection (synapse) between the neurons may facilitate a signal transmission from one neuron to another. The receiving (postsynaptic) neuron may process the signal and downstream neurons connected to it. Typically, neurons are organized in layers.

As shown in FIG. 8, the neural network model may include a plurality of layers. Different layers of the plurality of layers may perform different kinds of transformations based on their inputs. For example, a CNN model may include an input layer, a convolutional layer, a pooling layer, a full connected layer, etc. The input of the neural network model 810 may include at least one sample absorption contrast image. For example, each of $x_1, x_2, \ldots x_N$ may represent one of the at least one sample absorption contrast image. The output of the neural network model 820 may include at least one sample phase contrast image. For example, each of $y_1, y_2, \ldots y_m$ may represent one of the at least one sample phase contrast image. During a training process, the model may develop its inner structure or parameters of layers based on its input and output.

Figure 9A:
FIG. 9A is a schematic diagram illustrating an exemplary absorption contrast image according to some embodiments of the present disclosure.
Figure 9B:
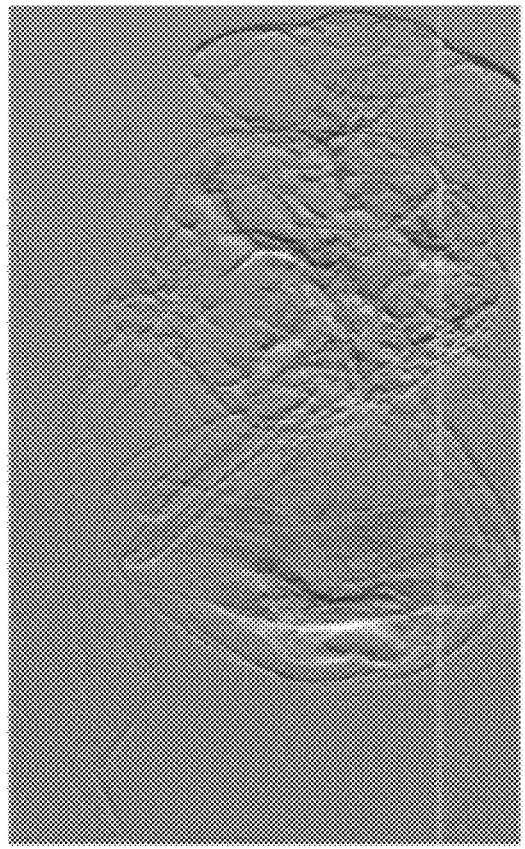
FIG. 9B is a schematic diagram illustrating an exemplary phase contrast image according to some embodiments of the present disclosure.

FIG. 9A and FIG. 9B are schematic diagrams illustrating an exemplary absorption contrast image and a corresponding phase contrast image, respectively. FIG. 9A shows an absorption contrast image obtained by scanning an object using an X-ray imaging device. FIG. 9B shows a phase contrast image generated by a method disclosed in the present disclosure (e.g., by executing the phase contrast image generation model based on the absorption contrast image in FIG. 9A). It can be seen that the phase contrast image shown in FIG. 9B has a better quality (e.g., higher signal-to-noise ratio, higher contrast) with respect to soft tissues than the absorption contrast image shown in FIG. 9A.

In some embodiments, the phase contrast image shown in FIG. 9B and the absorption contrast image shown in FIG. 9A may be used to train the preliminary model. In some embodiments, the processing device 140 (e.g., the processing module 430) may execute a phase contrast image generation model to generate the phase contrast image shown in FIG. 9B based on the absorption contrast image shown in FIG. 9A.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a specific feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the specific features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A system for generating a phase contrast image, comprising:
    a radioactive scanning source configured to emit radioactive rays toward a first object;
    a detector configured to detect at least some of the radioactive rays emitted from the radioactive scanning source impinging on the detector and to generate a plurality of readings based on the detected radioactive rays;
    a storage device storing a set of instructions, and
    at least one processor configured to communicate with the storage device, wherein when the at least one processor executes the set of instructions, the system is directed to:
        reconstruct an absorption contrast image of the first object based on the plurality of readings;
        obtain a phase contrast image generation model, wherein the phase contrast image generation model is trained based on at least one sample absorption contrast image and at least one sample phase contrast image of at least one second object; and
        execute the phase contrast image generation model to generate a phase contrast image of the first object based on the absorption contrast image of the first object.

2. The system of claim 1, wherein the absorption contrast image of the first object and the at least one sample absorption contrast image of the second object are obtained by scanning with a same scanning parameter and image reconstruction based on a same reconstruction parameter.

3. The system of claim 1, wherein the phase contrast image generation model is a neural network model.

4. The system of claim 1, wherein the system is further directed to:
    obtain a dark field image generation model; and
    execute the dark field image generation model based on the absorption contrast image or the phase contrast image of the first object to generate a dark field image of the first object,
    wherein the dark field image generation model is trained based on the at least one sample absorption contrast image of the second object and at least one sample dark field image of the at least one second object or based on the at least one sample phase contrast image of the at least one second object and the at least one sample dark field image of the at least one second object.

5. The system of claim 1, wherein the phase contrast image generation model is trained by a model training process, the model training process comprising:
    obtaining a preliminary model;
    obtaining at least one pair of training images of the at least one second object including the at least one sample absorption contrast image and the at least one sample phase contrast image of the at least one second object, wherein each of the at least one pair of the training image includes a sample absorption contrast image and a corresponding sample phase contrast image; and
    training the preliminary model based on the at least one pair of training images to generate a phase contrast image generation model.

6. The system of claim 5, wherein the obtaining the at least one pair of training images of the at least one second object comprises:
    for each of the at least one second object,
        obtaining a sample photon signal of the second object;

separating the sample photon signal into a sample absorption contrast signal and a sample phase contrast signal;
generating a sample absorption contrast image based on the sample absorption contrast signal; and
generating a corresponding sample phase contrast image based on the sample phase contrast signal.

7. The system of claim 6, wherein the obtaining the sample photon signal comprises:
scanning the at least one second object using a synchrotron light source.

8. The system of claim 6, wherein the at least one second object is a simulated object, and the obtaining the sample photon signal comprises:
performing at least one numerical simulation on the at least one second object to obtain the sample photon signal.

9. The system of claim 5, wherein the training the preliminary model based on the at least one pair of training images to generate the phase contrast image generation model comprises:
executing the preliminary model based on the sample absorption contrast image to generate at least one output image; and
training the preliminary model by minimizing the difference between the at least one output image and the corresponding sample phase contrast image to generate the phase contrast image generation model.

10. The system of claim 1, wherein the phase contrast image generation model is trained using a deep learning algorithm.

11. A method implemented on a computing device having a storage device storing a set of instructions for generating a phase contrast image and at least one processor communicated with the storage device, the method comprising:
obtaining an absorption contrast image of a first object;
obtaining a phase contrast image generation model, wherein the phase contrast image generation model is associated with at least one sample absorption contrast image and at least one sample phase contrast image of at least one second object; and
executing the phase contrast image generation model to generate a phase contrast image of the first object based on the absorption contrast image of the first object.

12. The method of claim 11, wherein the absorption contrast image of the first object and the at least one sample absorption contrast image of the second object are obtained by scanning with a same scanning parameter and image reconstruction based on a same reconstruction parameter.

13. The method of claim 11, wherein the phase contrast image generation model is a neural network model.

14. The method of claim 11, further comprising:
obtaining a dark field image generation model; and
executing the dark field image generation model based on the absorption contrast image or the phase contrast image of the first object to generate a dark field image of the first object,
wherein the dark field image generation model is trained based on the at least one sample absorption contrast image of the second object and at least one sample dark field image of the at least one second object or based on the at least one sample phase contrast image of the at least one second object and the at least one sample dark field image of the at least one second object.

15. The method of claim 11, wherein the phase contrast image generation model is trained by a model training process, the model training process comprising:
obtaining a preliminary model;
obtaining at least one pair of training images of the at least one second object including the at least one sample absorption contrast image and the at least one sample phase contrast image of the at least one second object, wherein each of the at least one pair of the training image includes a sample absorption contrast image and a corresponding sample phase contrast image; and
training the preliminary model based on the at least one pair of training images to generate a phase contrast image generation model.

16. The method of claim 15, wherein the obtaining the pair of training images of the at least one second object further comprises:
for each of the at least one second object,
obtaining a sample photon signal of the second object;
separating the sample photon signal into a sample absorption contrast signal and a sample phase contrast signal;
generating a sample absorption contrast image based on the sample absorption contrast signal; and
generating a corresponding sample phase contrast image based on the sample phase contrast signal.

17. The method of claim 16, wherein the obtaining the sample photon signal of the second object further comprises:
scanning the at least one second object using a synchrotron light source.

18. The method of claim 16, wherein the at least one second object is a simulated object, and the obtaining the sample photon signal further comprises:
performing at least one numerical simulation on the at least one second object to obtain the sample photon signal.

19. The method of claim 15, wherein the training the preliminary model based on the at least one pair of training images to generate the phase contrast image generation model further comprises:
executing the preliminary model based on the sample absorption contrast image to generate at least one output image; and
training the preliminary model by minimizing the difference between the at least one output image and the corresponding sample phase contrast image to generate the phase contrast image generation model.

20. A non-transitory computer readable medium, comprising executable instructions for generating a phase contrast image that, when executed by at least one processor of an electronic device, directs the at least one processor to perform actions comprising:
obtaining an absorption contrast image of a first object;
obtaining a phase contrast image generation model, wherein the phase contrast image generation model is associated with at least one sample absorption contrast image and at least one sample phase contrast image of at least one second object; and
executing the phase contrast image generation model to generate a phase contrast image of the first object based on the absorption contrast image of the first object.

* * * * *